United States Patent
Warren

(10) Patent No.: US 7,103,409 B2
(45) Date of Patent: *Sep. 5, 2006

(54) ATRIAL AND VENTRICULAR IMPLANTABLE CARDIOVERTER-DEFIBRILLATOR AND LEAD SYSTEM

(75) Inventor: Jay A. Warren, North Oaks, MN (US)

(73) Assignee: Cardiac Pacemakers, Inc., Saint Paul, MN (US)

( * ) Notice: Subject to any disclaimer, the term of this patent is extended or adjusted under 35 U.S.C. 154(b) by 486 days.

This patent is subject to a terminal disclaimer.

(21) Appl. No.: 10/434,612

(22) Filed: May 9, 2003

(65) Prior Publication Data

US 2003/0195576 A1 Oct. 16, 2003

Related U.S. Application Data

(60) Continuation of application No. 09/558,288, filed on Apr. 25, 2000, now Pat. No. 6,574,505, which is a division of application No. 09/130,087, filed on Aug. 7, 1998, now Pat. No. 6,067,471.

(60) Provisional application No. 60/055,176, filed on Aug. 8, 1997.

(51) Int. Cl.
*A61N 1/362* (2006.01)

(52) U.S. Cl. .......................................................... 607/5

(58) Field of Classification Search ............... 607/5–14
See application file for complete search history.

(56) References Cited

U.S. PATENT DOCUMENTS

| | | | |
|---|---|---|---|
| 3,738,370 A | 6/1973 | Charms | 128/419 |
| 3,942,536 A | 3/1976 | Mirowski et al. | 128/419 D |
| 3,952,750 A | 4/1976 | Mirowski et al. | 128/419 |
| 4,030,509 A | 6/1977 | Heilman et al. | 128/419 D |
| 4,161,952 A | 7/1979 | Kinney et al. | 128/786 |
| 4,270,549 A | 6/1981 | Heilman | |
| 4,291,707 A | 9/1981 | Heilman et al. | |
| 4,481,953 A | 11/1984 | Gold et al. | 128/786 |
| 4,567,900 A | 2/1986 | Moore | |
| 4,708,145 A | 11/1987 | Tacker, Jr. et al. | 128/419 D |
| 4,727,877 A | 3/1988 | Kallok | 128/419 |
| 4,865,037 A | 9/1989 | Chin et al. | |

(Continued)

FOREIGN PATENT DOCUMENTS

EP         0326290        8/1989

(Continued)

OTHER PUBLICATIONS

Fain, et al., "A New Internal Defibrillation Lead System: Intrapericardial Placement Without Thoracotomy", *Circulation Supplement*, 76 (4), Abstracts from the 60th Scientific Sessions, Abstract No. 1839,(Oct. 1987),1 p.

(Continued)

*Primary Examiner*—Scott M. Getzow
(74) *Attorney, Agent, or Firm*—Schwegman, Lundberg, Woessner & Kluth, P.A.

(57) ABSTRACT

A cardiac rhythm management system, such as an implantable cardioverter-defibrillator (ICD), provides atrial anti-tachyarrhythmia therapy, such as a bipolar or unipolar electrical cardioversion countershock, or provides both atrial and ventricular anti-tachyarrhythmia therapy. The atrial and ventricular anti-tachyarrhythmia therapies have independent cardioversion-defibrillation energy levels and other parameters. The system provides an endocardial lead that is convenient to implant for providing the anti-tachyarrhythmia therapy. The endocardial lead includes a first supraventricular electrode disposed in the atrium and superior vena cava, and optionally includes a first ventricular electrode and ICD housing electrode.

28 Claims, 7 Drawing Sheets

U.S. PATENT DOCUMENTS

| | | | |
|---|---|---|---|
| 4,905,691 A | 3/1990 | Rydell | |
| 4,922,927 A | 5/1990 | Fine et al. | 128/786 |
| 4,934,049 A | 6/1990 | Kiekhafer et al. | 29/883 |
| 4,938,231 A | 7/1990 | Milijasevic et al. | |
| 4,971,070 A | 11/1990 | Holleman et al. | |
| 5,020,544 A | 6/1991 | Dahl et al. | |
| 5,042,143 A | 8/1991 | Holleman et al. | 29/825 |
| 5,099,838 A | 3/1992 | Bardy | 128/419 D |
| 5,105,826 A | 4/1992 | Smits et al. | |
| 5,165,403 A | 11/1992 | Mehra | 128/419 D |
| 5,292,338 A | 3/1994 | Bardy | 607/5 |
| 5,300,110 A | 4/1994 | Latterell et al. | |
| 5,306,291 A | 4/1994 | Kroll et al. | 607/5 |
| 5,314,430 A | 5/1994 | Bardy | 607/5 |
| 5,379,776 A | 1/1995 | Murphy et al. | 128/705 |
| 5,391,199 A | 2/1995 | Ben-Haim | 607/122 |
| 5,480,422 A | 1/1996 | Ben-Haim | 607/122 |
| 5,509,925 A | 4/1996 | Adams et al. | 607/5 |
| 5,514,161 A | 5/1996 | Limousin | 607/9 |
| 5,531,781 A | 7/1996 | Alferness et al. | |
| 5,545,205 A | 8/1996 | Schulte et al. | 607/123 |
| 5,549,642 A | 8/1996 | Min et al. | 607/5 |
| 5,645,082 A | 7/1997 | Sung et al. | 128/897 |
| 5,683,429 A | 11/1997 | Mehra | 602/14 |
| 5,685,322 A | 11/1997 | Sung et al. | 128/897 |
| 5,713,926 A | 2/1998 | Hauser et al. | 607/5 |
| 5,718,241 A | 2/1998 | Ben-Haim et al. | 128/702 |
| 5,730,142 A | 3/1998 | Sun et al. | 128/705 |
| 5,738,096 A | 4/1998 | Ben-Haim | 128/653.1 |
| 5,772,604 A | 6/1998 | Langberg et al. | 600/518 |
| 5,782,876 A | 7/1998 | Flammang | 607/4 |
| 5,800,466 A | 9/1998 | Routh et al. | 607/14 |
| 5,836,985 A | 11/1998 | Rostami et al. | 607/14 |
| 5,840,025 A | 11/1998 | Ben-Haim | 600/424 |
| 5,881,732 A | 3/1999 | Sung et al. | 128/898 |
| 6,067,471 A * | 5/2000 | Warren | 607/5 |
| 6,280,462 B1 | 8/2001 | Hauser et al. | 607/5 |
| 6,574,505 B1 * | 6/2003 | Warren | 607/5 |

FOREIGN PATENT DOCUMENTS

| | | |
|---|---|---|
| GB | 2032278 | 6/1980 |
| WO | WO-89/06148 | 7/1989 |

OTHER PUBLICATIONS

Feeser, S A., et al., "Strength-duration and probability of success curves for defibrillation with biphasic waveforms", *Circulation*, 82 (6), (Dec. 1990), 2128-2141.

Tang, et al., "Ventricular Defibrillation Using Biphasic Waveforms: The Importance of Phasic Duration", *Journal of the American College of Cardiology*, 13 (1), (Jan. 1989), pp. 207-214.

Wessale, et al., "Bipolar Catheter Defibrillation in Dogs Using Trapezoidal Waveforms of Various Tilts", *Journal of Electrocardiology*, 13(4), (1980), pp. 359-365.

* cited by examiner

ATRIAL AND VENTRICULAR IMPLANTABLE CARDIOVERTER-DEFIBRILLATOR AND LEAD SYSTEM

CROSS-REFERENCE TO RELATED APPLICATION(S)

This application is a continuation of U.S. patent application Ser. No. 09/558,288, filed on Apr. 25, 2000, now U.S. Pat. No. 5,574,505 which is a division of U.S. patent application Ser. No. 09/130,087, filed on Aug. 7, 1998, now issued as U.S. Pat. No. 6,067,471, which claims the benefit under 35 U.S.C. §119(e) of U.S. Provisional Application No. 60/055,176, filed on Aug. 8, 1997, the specifications of which are incorporated herein by reference.

TECHNICAL FIELD OF THE INVENTION

This invention relates generally to cardiac rhythm management systems, and more particularly to an implantable cardioverter-defibrillator and lead system for treating atrial tachyarrhythmias or treating both atrial and ventricular tachyarrhythmias.

BACKGROUND OF THE INVENTION

Atrial tachyarrhythmias are quite common, and occur even in patients who are not acutely ill. One such atrial tachyarrhythmia, atrial fibrillation, does not usually pose an immediate threat to the patient's life, but since prolonged atrial fibrillation can compromise patient hemodynamics, its treatment is highly desirable. For patients having episodes of atrial fibrillation that do not respond to drug therapy, an electrical countershock delivered by an implantable cardioverter-defibrillator (ICD) may be used to convert the atrial tachyarrhythmia into a normal heart rhythm.

One method of delivering an electrical countershock to treat atrial fibrillation is illustrated in the Bardy U.S. Pat. No. 5,314,430. The Bardy patent describes a lead system having a coronary sinus/great vein electrode and a subcutaneous left pectoral plate electrode such as on a surface of a defibrillator housing. The Bardy lead system optionally includes a superior vena cava and/or ventricular electrode. The Bardy lead system can be employed in a device that is intended to perform atrial cardioversion or defibrillation only, or in a device that also performs ventricular cardioversion or defibrillation. However, placing the electrode in the coronary/sinus great vein portion of the heart is an extremely difficult procedure for the implanting physician. Moreover, in the case where both atrial cardioversion and ventricular defibrillation are desired, a separate ventricular lead is required. Therefore, there is a need in the art for a more convenient system for performing either atrial cardioversion or both atrial cardioversion and ventricular defibrillation.

SUMMARY OF THE INVENTION

A cardiac rhythm management system includes a method of applying anti-tachyarrhythmia therapy to a heart in a patient. In one form of the cardiac rhythm management system, a first ventricular electrode is disposed in a ventricle of the heart. A first supraventricular electrode is disposed in a supraventricular region of the heart. The system monitors atrial heart activity for atrial tachyarrhythmia activity indicative of a need for the anti-tachyarrhythmia therapy. Anti-tachyarrhythmia therapy is applied through the first supraventricular and first ventricular electrodes if atrial tachyarrhythmia activity needing anti-tachyarrhythmia therapy is detected.

In another form of the cardiac rhythm management system, an implantable cardioverter-defibrillator (ICD) is disposed in a patient, such as in a pectoral region. The ICD includes an ICD housing electrode. A first supraventricular electrode is disposed in a supraventricular region of the heart. The system monitors atrial heart activity for atrial tachyarrhythmia activity indicative of a need for the anti-tachyarrhythmia therapy. Anti-tachyarrhythmia therapy is applied through the first supraventricular electrode and the ICD housing electrode if atrial tachyarrhythmia activity needing anti-tachyarrhythmia therapy is detected.

In one embodiment, the implantable cardiac rhythm management system includes a first supraventricular electrode, proportioned for disposition within a supraventricular region of the heart. A first ventricular electrode is proportioned for disposition within a ventricle of the heart. An ICD device is electrically coupled for delivering the anti-tachyarrhythmia therapy through the first supraventricular and first ventricular electrodes in response to atrial heart activity indicating a need for anti-tachyarrhythmia therapy.

In another embodiment, the implantable cardiac rhythm management system includes a first supraventricular electrode, proportioned for disposition within a supraventricular region of the heart. An ICD device is electrically coupled to the first supraventricular electrode. An ICD housing electrode is included, carried on a housing of the ICD device and coupled to the ICD device. The ICD device delivers anti-tachyarrhythmia therapy through the ICD housing electrode and the first supraventricular electrode in response to atrial heart activity indicating a need for anti-tachyarrhythmia therapy.

Thus, the cardiac rhythm management system provides either atrial or both atrial and ventricular anti-tachyarrhythmia therapy through a single endocardial lead, although a separate lead may also be used, such as for sensing heart activity. In addition to providing dual-chamber anti-tachyarrhythmia therapy through a single endocardial lead, the cardiac rhythm management system avoids the need for the difficult placement of an electrode in the coronary sinus/great vein region. As a result, the convenience of the lead placement procedure by the implanting physician is greatly increased.

BRIEF DESCRIPTION OF THE DRAWINGS

In the drawings, like numerals describe substantially similar components throughout the several views.

DETAILED DESCRIPTION OF THE INVENTION

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized and that structural, logical and electrical changes may be made without departing from the scope of the present invention. The following detailed description is, therefore, not to be taken in a limiting sense, and the scope of the present invention is defined by the appended claims and their equivalents. In the accompanying drawings, like numerals describe substantially similar components throughout the several views.

The present invention relates to applying anti-tachyarrhythmia therapy to a heart, including to an atrium of the heart. In this application, atrial tachyarrhythmias (ATs) are understood to comprise any atrial tachyarrhythmia including, but not limited to: sinus tachycardia, atrial flutter, atrial tachycardia, atrial fibrillation, AV nodal reentrant tachycardia. Ventricular tachyarrhythmias (VTs) are understood to comprise any ventricular tachyarrhythmia including, but not limited to, ventricular tachycardia, and ventricular fibrillation (VF). Cardioversion and defibrillation are understood to refer generally to any treatment of a cardiac arrhythmia by an electrical countershock. Cardioverter and defibrillator are understood to refer generally to any device capable of treating a cardiac arrhythmia through an electrical countershock, though pacing or other therapy may also be included. Anti-tachyarrhythmia therapy is understood to comprise treatment of atrial tachyarrhythmia by electrical countershock, anti-tachyarrhythmia drugs, or anti-tachycardia pacing.

The present invention provides a system for delivering anti-tachyarrhythmia therapy, such as an implantable cardioverter-defibrillator (ICD) delivering an electrical countershock through a lead system that is convenient to implant. In one embodiment, a countershock is delivered to an atrium needing anti-tachyarrhythmia therapy. In another embodiment, a countershock is delivered to either an atrium needing anti-tachyarrhythmia therapy or to a ventricle needing anti-tachyarrhythmia therapy.

Figure 1:
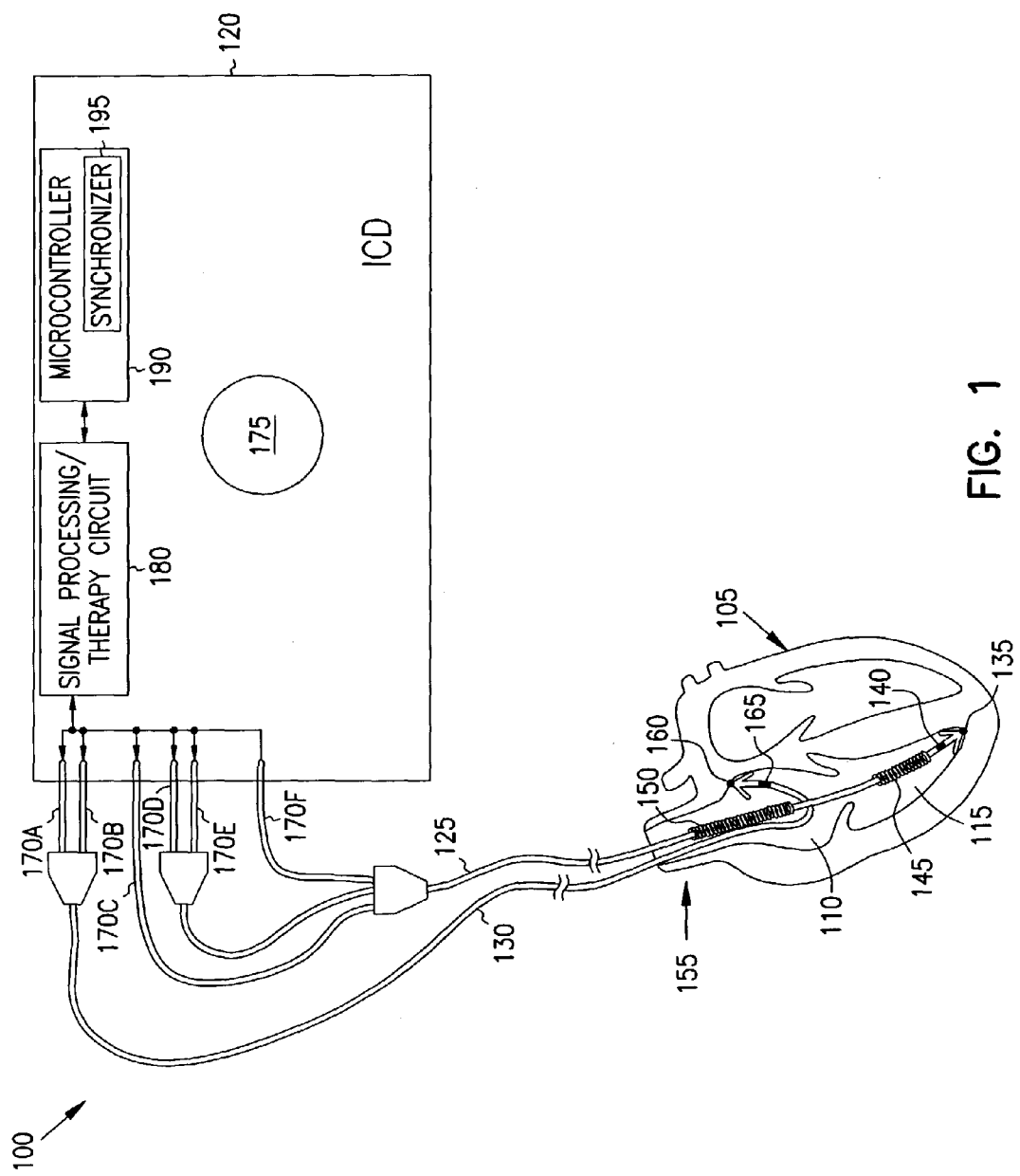
FIG. 1 is a schematic/block diagram illustrating generally one embodiment of a cardiac rhythm management system in relation to a heart to which it delivers therapy.

FIG. 1 is a schematic/block diagram illustrating generally one embodiment of a cardiac rhythm management system 100 in relation to a heart 105 to which it delivers therapy. Heart 105 includes an atrium 110, such as a right atrium, and a ventricle 115, such as a right ventricle. Cardiac rhythm management system 100 includes an implantable cardioverter-defibrillator (ICD) 120, a first lead 125, and a second lead 130.

First lead 125 includes a distal sensing electrode, such as tip electrode 135, and a proximal sensing electrode, such as ring electrode 140. Tip electrode 135 and ring electrode 140 of first lead 125 are proportioned for disposition in the ventricle 115, and illustrate one embodiment of a ventricular sensor for sensing ventricular heart activity, or for sensing ventricular heart activity and also delivering ventricular pacing therapy. First lead 125 also includes a distal defibrillation electrode 145 that is proportioned for disposition in ventricle 115 for delivery of an electrical countershock to heart 105, as described below. First lead 125 further includes a proximal defibrillation electrode 150 that is proportioned for disposition in a supraventricular region of heart 105, such as within the superior portion of atrium 110 and within superior vena cava 155 extending therefrom, for delivery of an electrical countershock to heart 105, as described below.

One example embodiment of first lead 125 is an endocardial defibrillation lead that is described in the Schulte et al. U.S. Pat. No. 5,545,205, which is assigned to the assignee of the present application and which is herein incorporated by reference. In another example embodiment, first lead 125 is an endocardial defibrillation lead that is sold under the brand name "Endotak DSP" and Model Numbers 0090, 0092, and 0094 by the assignee of the present application. A further example embodiment of first lead 125 is an endocardial defibrillation lead that is sold under the brand name "Endotak C" and Model Numbers 0070, 0072, 0074, 0060, 0062, and 0064 by the assignee of the present application.

Second lead 130 includes a distal electrode, such as tip electrode 160, and a proximal electrode, such as ring electrode 165. Tip electrode 160 and ring electrode 165 of second lead 130 are proportioned for disposition in atrium 110, and illustrate one embodiment of an atrial sensor for sensing atrial heart activity, or for sensing atrial heart activity and also delivering atrial pacing therapy. In one example embodiment, second lead 130 is an endocardial pacing/sensing lead such as a bipolar atrial J lead that is sold as Model Number 4271 by the assignee of the present application. In another example embodiment, second lead 130 is an endocardial pacing/sensing lead such as a positive fixation bipolar lead that is sold under the brand name "Sweet Tip" and Model Number 4269 by the assignee of the present application.

ICD 120 is subcutaneously implanted in the patient, such as in a pectoral or an abdominal region or elsewhere. First lead 125 and second lead 130 are each coupled to ICD 120, such as through receptacles 170A–F. One embodiment of ICD 120 includes an ICD housing electrode 175, integrally formed with the housing of ICD 120, for unipolar sensing of atrial or ventricular heart activity signals, or for unipolar delivery of atrial or ventricular pacing therapy, countershock therapy, or the atrial or ventricular delivery of both pacing and countershock therapy.

In the embodiment of the cardiac rhythm management system 100 illustrated in FIG. 1, ICD 120 includes a signal processing/therapy circuit 180 and a microcontroller 190. Signal processing/therapy circuit 180 receives and processes heart activity signals, such as from the receptacles 170A–F that are coupled to tip electrode 135 and ring electrode 140 of first lead 125 or coupled to tip electrode 160 and ring electrode 165 of second lead 130. Signal processing/therapy circuit 180 also provides electrical countershock therapy to heart 105, as described below, such as a low energy cardioversion countershock or a higher energy defibrillation countershock. The electrical countershock therapy is delivered to heart 105 via distal defibrillation electrode 145, proximal defibrillation electrode 150, or ICD housing electrode 175. In one embodiment, signal processing/therapy circuit 180 provides pacing therapy to heart 105, such as via tip electrode 135 of first lead 125, ring electrode 140 of first lead 125, tip electrode 160 of second lead 130, ring electrode 165 of second lead 130, or ICD housing electrode 175. Microcontroller 190 controls the timing and delivery of the above-described pacing and countershock therapy to heart 105 in response to the above-described heart activity signals received and processed by signal processing/therapy circuit 180. In one embodiment, microcontroller 190 includes a synchronizer 195 for synchronizing delivery of anti-tachyarrhythmia therapy to a ventricular activation of the heart. Synchronizer 195 may be implemented either in hardware, as a sequence of instructions on microcontroller 190, or by any other suitable synchronization technique.

Figure 2:
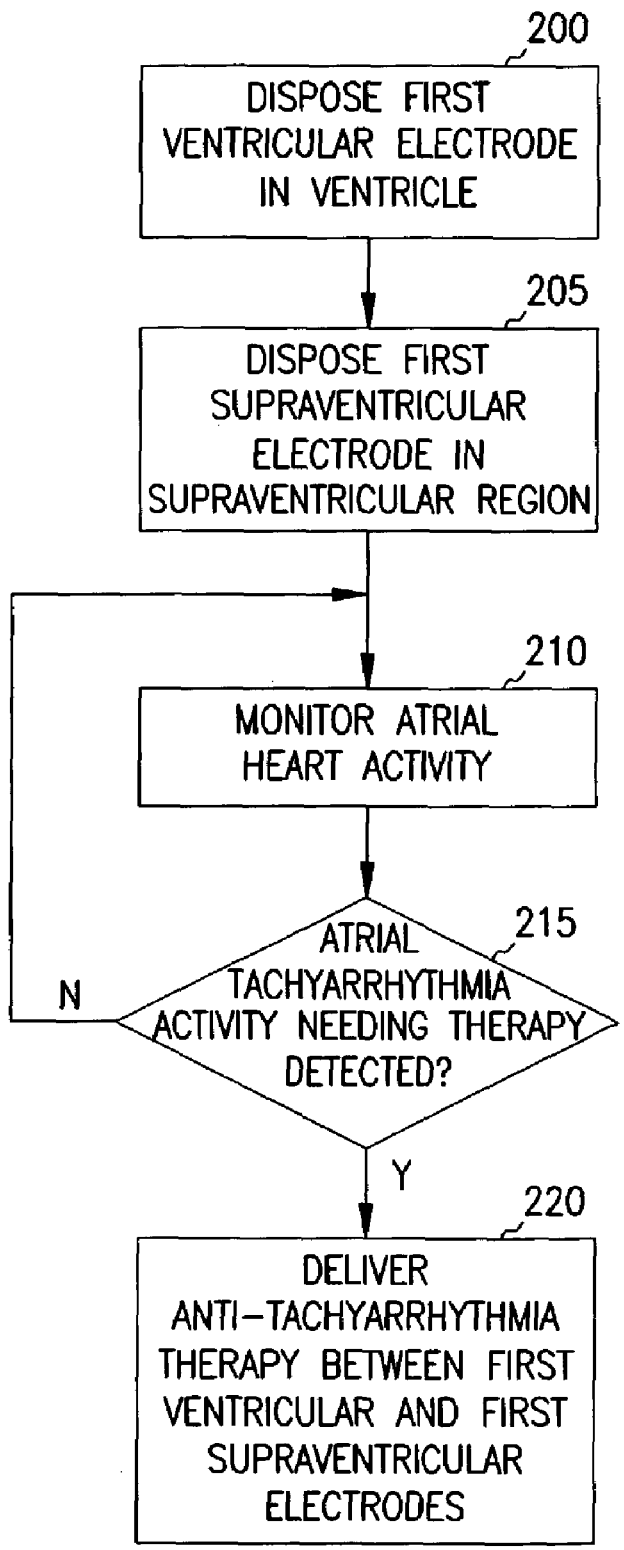
FIG. 2 is a flow chart illustrating generally one embodiment of a method of applying anti-tachyarrhythmia therapy.

FIG. 2 is a flow chart illustrating generally one embodiment of a method of applying anti-tachyarrhythmia therapy to heart 105 according to the present invention. At step 200, a first ventricular electrode, such as distal defibrillation electrode 145, is disposed in ventricle 115 of heart 105, such as by transvenous introduction of first lead 125. At step 205, a first supraventricular electrode, such as proximal defibrillation electrode 150 introduced transvenously by implantation of first lead 125, is disposed in a supraventricular region of heart 105, such as within atrium 110 or within both atrium 110 and superior vena cava 155 extending therefrom. At step 210, atrial heart activity (i.e., electrical signals intrinsic to the region of heart 105 in or near atrium 110) is monitored, such as by ICD 120, for the above-described atrial tachyarrhythmia activity. If atrial tachyarrhythmia activity indicative of a need for anti-tachyarrhythmia therapy is detected at step 215, the anti-tachyarrhythmia therapy is delivered at step 220 through the first supraventricular and first ventricular electrodes. In one embodiment, the anti-tachyarrhythmia therapy includes a biphasic cardioversion countershock having an energy of approximately between 1 and 10 Joules. The actual countershock energy delivered may depend upon the particular placement of first lead 125, the particular waveform of the cardioversion countershock, or other factors. Other countershock waveforms that are used include, but are not limited to, monophasic and triphasic.

Figure 3:
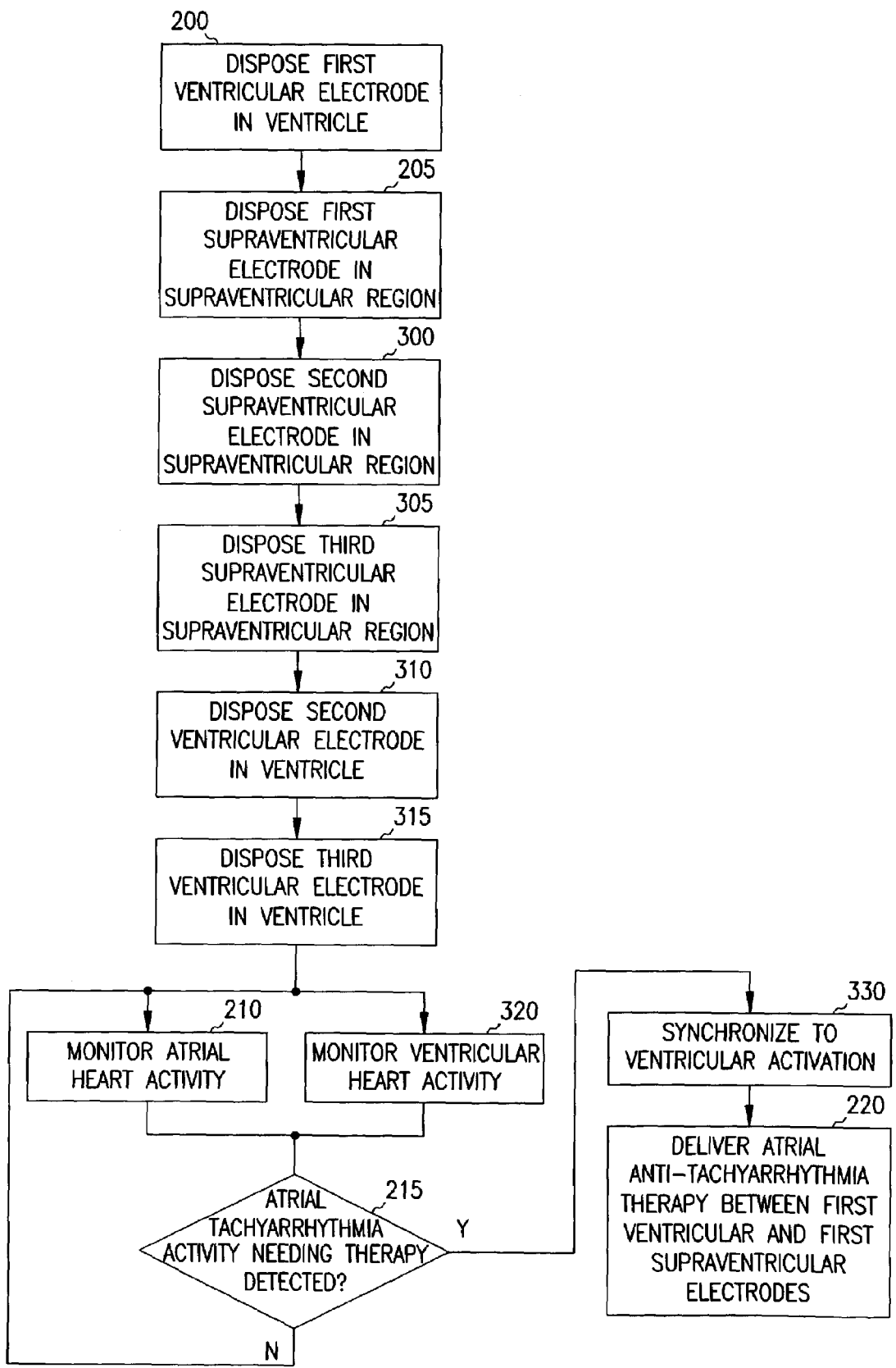
FIG. 3 is a flow chart illustrating generally a second embodiment of a method of applying anti-tachyarrhythmia therapy.

FIG. 3 is a flow chart illustrating generally another embodiment of a method of applying anti-tachyarrhythmia therapy to heart 105 according to the present invention. At step 200, a first ventricular electrode is disposed in ventricle 115, as described above. At step 205, a first supraventricular electrode, is disposed in a supraventricular region of heart 105, as described above.

At step 300, a second supraventricular electrode, such as tip electrode 160 of second lead 130, is disposed in the supraventricular region of heart 105, such as in atrium 110, by transvenous introduction of second lead 130. At step 305, a third supraventricular electrode, such as ring electrode 165 of second lead 130, is disposed in the supraventricular region of heart 105, such as in atrium 110, by transvenous introduction of second lead 130. At step 310, a second ventricular electrode, such as tip electrode 135 of first lead 125, is disposed in ventricle 115, such as by transvenous introduction of first lead 125. At step 315, a third ventricular electrode, such as ring electrode 140 of first lead 125, is disposed in ventricle 115, such as by transvenous introduction of first lead 125.

At step 210, atrial heart activity is monitored, as described above, such as by bipolar sensing of atrial heart activity through tip electrode 160 and ring electrode 165 of second lead 130. Another embodiment of step 210 includes unipolar sensing of atrial heart activity through ICD housing electrode 175 and either of tip electrode 160 and ring electrode 165 of second lead 130.

At step 320, which maybe concurrent with step 210, ventricular heart activity (i.e., electrical signals intrinsic to the region of heart 105 in or near ventricle 115) is monitored, such as by ICD 120, for ventricular activations causing ventricular depolarizations of heart 105. One embodiment of step 320 includes bipolar sensing of ventricular heart activity through tip electrode 135 and ring electrode 140 of first lead 125. Another embodiment of step 320 includes bipolar sensing of ventricular heart activity through tip electrode 135 and distal defibrillation electrode 145, such that step 315 of disposing the third ventricular electrode may be eliminated. Another embodiment of step 320 includes unipolar sensing of ventricular heart activity through ICD housing electrode 175 and either of tip electrode 135, ring electrode 140, or distal defibrillation electrode 145 of first lead 125. For example, if step 320 includes unipolar sensing of ventricular heart activity through ICD housing electrode 175 and distal defibrillation electrode 145 of first lead 125, the steps 310 and 315 of respectively disposing second and third ventricular electrodes may be eliminated.

If atrial tachyarrhythmia activity indicative of a need for anti-tachyarrhythmia therapy is detected at step 215, ICD 120 synchronizes to a ventricular activation at step 330 before delivering at step 220 the anti-tachyarrhythmia therapy to heart 105 through the first supraventricular and first ventricular electrodes. If no atrial tachyarrhythmia activity indicative of a need for anti-tachyarrhythmia therapy is detected at step 215, the monitoring of atrial and ventricular heart activity continues at respective steps 210 and 320.

Figure 4:
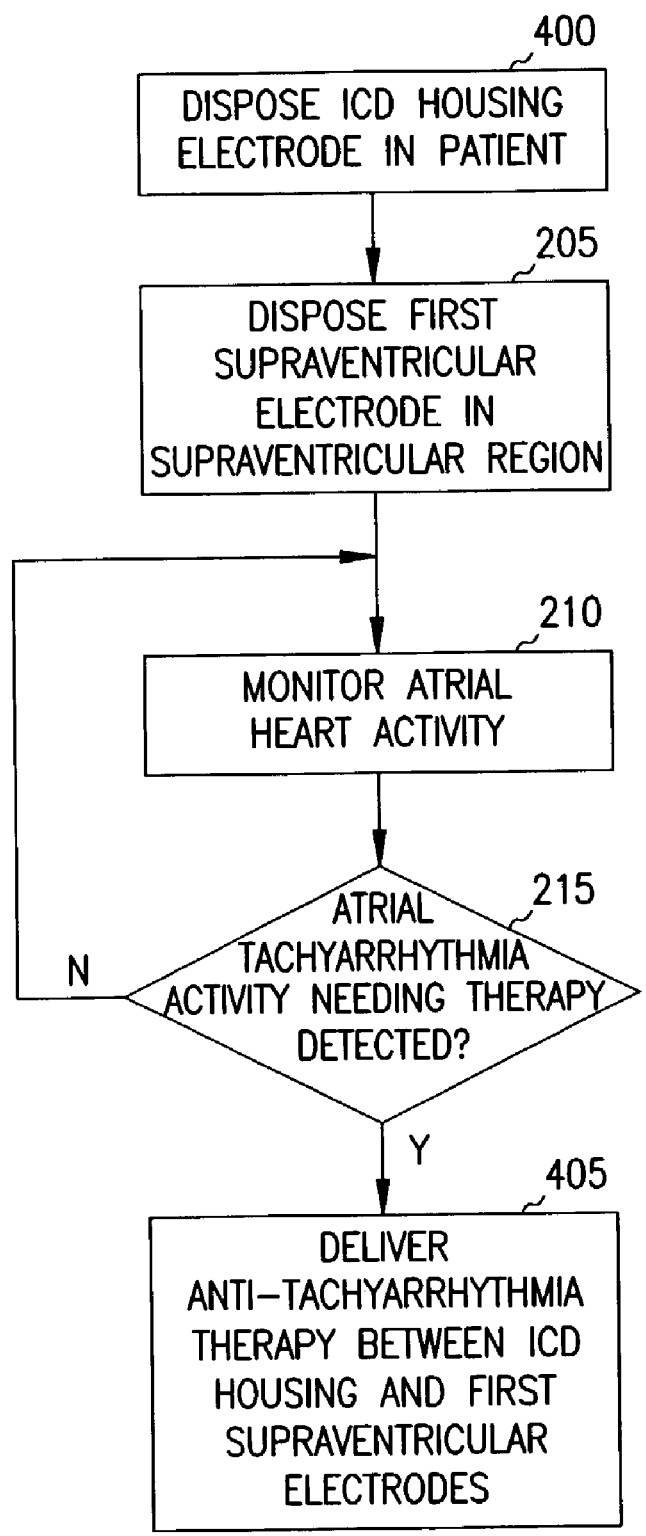
FIG. 4 is a flow chart illustrating generally a third embodiment of a method of applying anti-tachyarrhythmia therapy.

FIG. 4 is a flow chart illustrating generally another embodiment of a method of applying anti-tachyarrhythmia therapy to heart 105 according to the present invention. The method of FIG. 4 is similar to that of FIG. 2, except that no first ventricular electrode is needed in the method of FIG. 4. In the method of FIG. 4, however, ICD housing electrode 175 is disposed in the patient at step 400, such as by implantation within the pectoral region. If atrial tachyarrhythmia activity indicative of a need for anti-tachyarrhythmia therapy is detected at step 215, the anti-tachyarrhythmia therapy is delivered at step 405 through the first supraventricular electrode and ICD housing electrode 175. In one embodiment, the anti-tachyarrhythmia therapy includes a biphasic cardioversion countershock having an energy of approximately between 1 and 10 Joules. The actual countershock energy delivered may depend upon the particular placement of first lead 125 and ICD housing electrode 175, the particular waveform of the cardioversion countershock, or other factors. Other countershock waveforms that are used include, but are not limited to, monophasic and triphasic.

Figure 5:
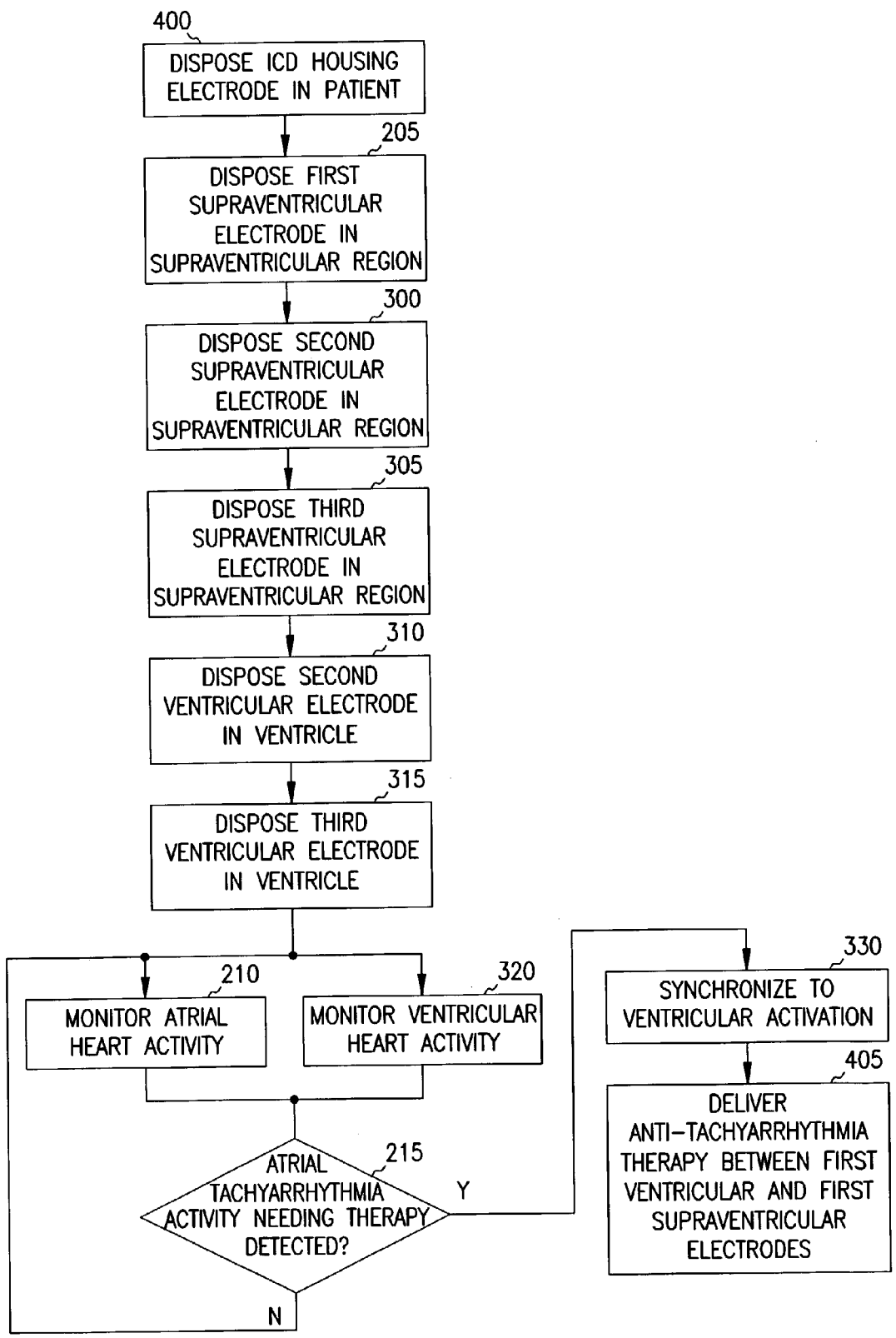
FIG. 5 is a flow chart illustrating generally a fourth embodiment of a method of applying anti-tachyarrhythmia therapy.

FIG. 5 is a flow chart illustrating generally another embodiment of a method of applying anti-tachyarrhythmia therapy to heart 105 according to the present invention. The method of FIG. 5 is similar to that of FIG. 3, except that no first ventricular electrode is needed in the method of FIG. 5. In the method of FIG. 5, however, ICD housing electrode 175 is disposed in the patient at step 400, such as by implantation within the pectoral region, abdominal region, or elsewhere. At step 320, sensing of ventricular heart activity is typically through tip electrode 135 and ring electrode 140 of first lead 125, or through tip electrode 135 and ICD housing electrode 175, where distal defibrillation electrode 145 is omitted. Alternatively, a tip electrode 135 may be introduced into ventricle 115 by a separate lead with first lead 125 configured to extend only into the supraventricular region of heart 105. In the method of FIG. 5, if atrial tachyarrhythmia activity indicative of a need for anti-tachyarrhythmia therapy is detected at step 215, ICD 120 synchronizes to a ventricular activation at step 330 before delivering to heart 105 at step 405 the anti-tachyarrhythmia therapy through the first supraventricular electrode and ICD housing electrode 175.

Figure 6:
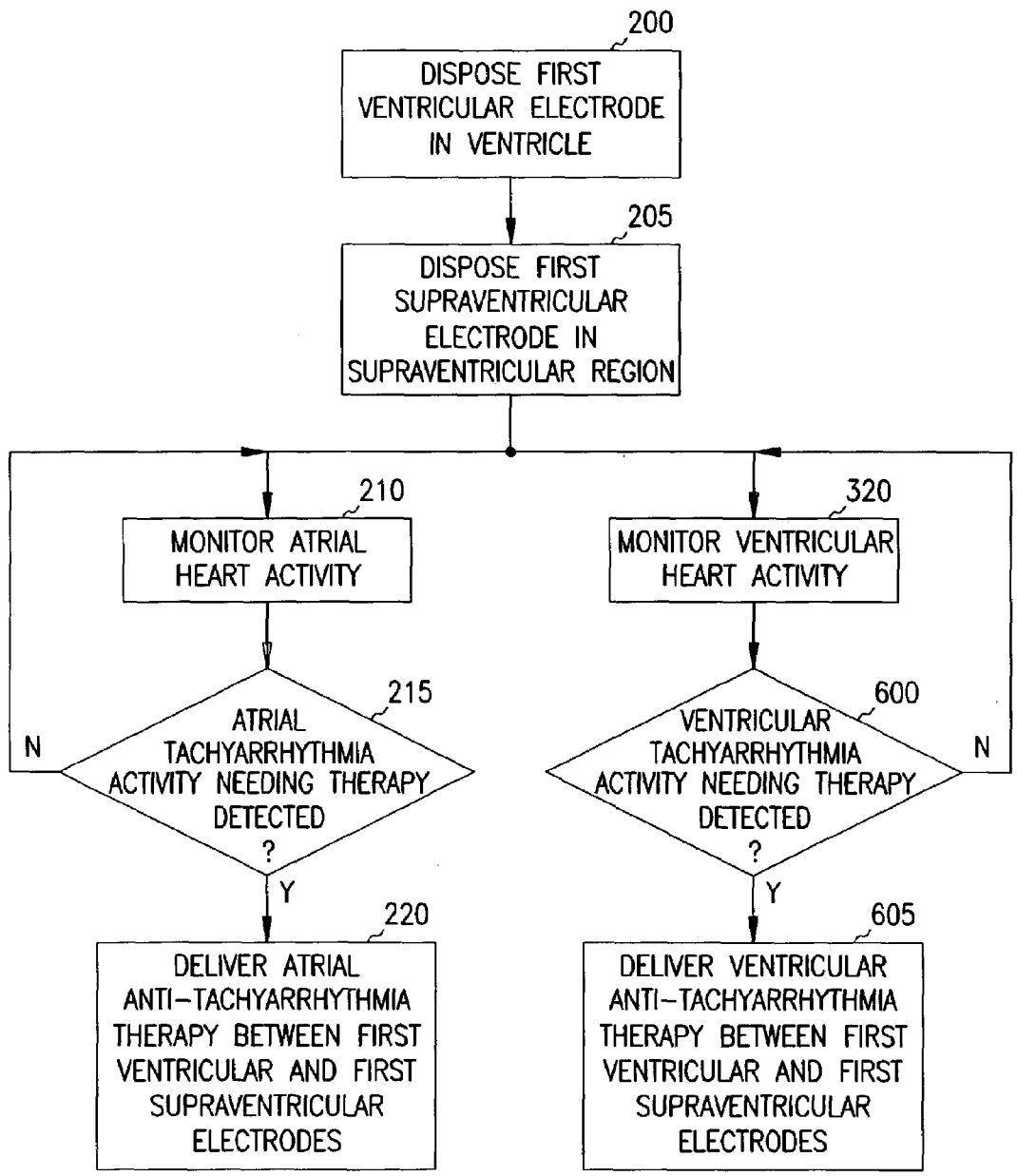
FIG. 6 is a flow chart illustrating generally a fifth embodiment of a method of applying anti-tachyarrhythmia therapy.

FIG. 6 is a flow chart illustrating generally another embodiment of a method of applying anti-tachyarrhythmia therapy to heart 105 according to the present invention. The method of FIG. 6 is similar to that of FIG. 2, except that the method of FIG. 6 delivers ventricular anti-tachyarrhythmia therapy in response to ventricular tachyarrhythmia activity needing such therapy. At step 320 of FIG. 6, ventricular heart activity is monitored, as described above, such as concurrently with the monitoring of atrial heart activity at step 210. If ventricular tachyarrhythmia activity indicative of a need for anti-tachyarrhythmia therapy is detected at step 600, the anti-tachyarrhythmia therapy is delivered at step 605 through the first supraventricular and first ventricular electrodes. In one embodiment, the ventricular anti-tachyarrhythmia therapy delivered at step 605 includes a biphasic defibrillation countershock having an energy of approximately between 1 and 10 Joules. The actual countershock energy delivered may depend upon the particular placement of first lead 125, the particular waveform of the cardioversion countershock, or other factors. Other countershock waveforms that are used include, but are not limited to, monophasic and triphasic.

Figure 7:
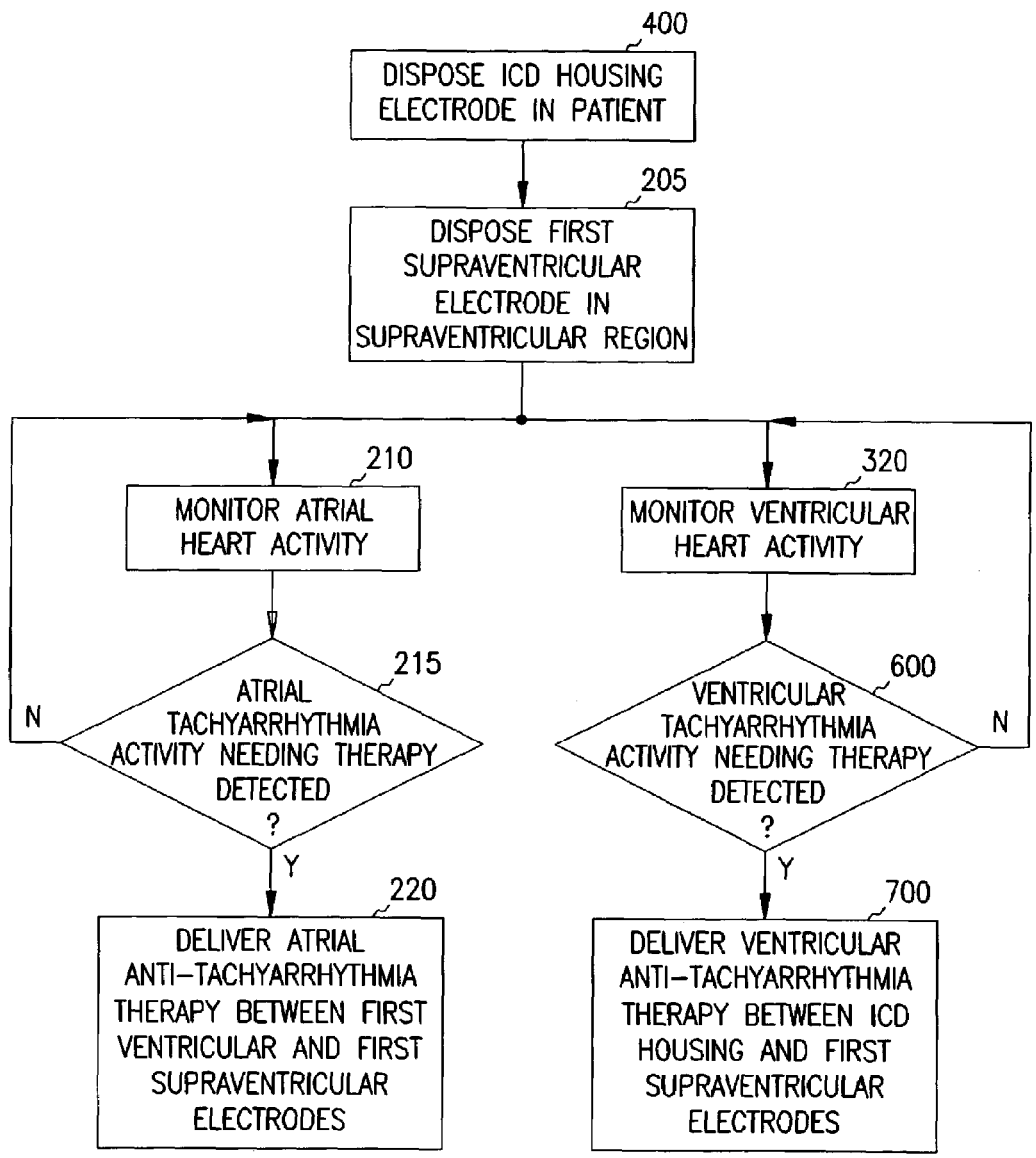
FIG. 7 is a flow chart illustrating generally a sixth embodiment of a method of applying anti-tachyarrhythmia therapy.

FIG. 7 is a flow chart illustrating generally another embodiment of a method of applying anti-tachyarrhythmia therapy to heart 105 according to the present invention. The method of FIG. 7 is similar to that of FIG. 6, except that the method of FIG. 7 provides unipolar delivery of ventricular anti-tachyarrhythmia therapy in response to ventricular tachyarrhythmia activity needing such therapy. At step 400, an ICD housing electrode 175 is disposed in the patient, as described above. If ventricular tachyarrhythmia activity indicative of a need for anti-tachyarrhythmia therapy is detected at step 600, the anti-tachyarrhythmia therapy is delivered to heart 105 at step 700 through the first supraventricular electrode and ICD housing electrode 175. In one embodiment, the ventricular anti-tachyarrhythmia therapy delivered at step 700 includes a biphasic defibrillation countershock having an energy of approximately between 1 and 10 Joules. The actual countershock energy delivered may depend upon the particular placement of first lead 125 and ICD housing electrode 175, the particular waveform of the cardioversion countershock, or other factors. Other countershock waveforms that are used include, but are not limited to, monophasic and triphasic.

Referring again to the cardiac rhythm management system of FIG. 1, it is understood that though first lead 125 has been described above with reference to tip electrode 135, ring electrode 140, distal defibrillation electrode 145, and proximal defibrillation electrode 150, certain embodiments of cardiac rhythm management system 100 need not include all of these electrodes. In one example embodiment of cardiac rhythm management system 100, ring electrode 140 is omitted, such as where sensing of ventricular heart activity is not needed, or where the sensing of ventricular heart activity is performed through tip electrode 135 and distal defibrillation electrode 145. In another example embodiment of cardiac rhythm management system 100, ring electrode 140 and tip electrode 135 are omitted, such as where sensing of ventricular heart activity is not needed, or where the sensing of ventricular heart activity is through distal defibrillation electrode 145 and proximal defibrillation electrode 150. In a further example embodiment of cardiac rhythm management system 100, ring electrode 140, tip electrode 135, and distal defibrillation electrode 145 are omitted, such as where cardiac rhythm management system 100 is used exclusively for providing atrial anti-tachyarrhythmia therapy through proximal defibrillation electrode 150 and ICD housing electrode 175. In this example, first lead 125 need not extend beyond the supraventricular region of heart 105 into ventricle 115 if no sensing of ventricular heart activity is needed. It is also understood that the electrodes carried by second lead 130 could be integrated with first lead 125 such that no separate second lead 130 is needed.

Thus, the present invention includes a cardiac rhythm management system 100 providing a device and method for delivering atrial anti-tachyarrhythmia therapy, or for delivering both atrial and ventricular anti-tachyarrhythmia therapy. One advantage of cardiac rhythm management system 100 is the use of first lead 125 and the first supraventricular electrode (i.e., proximal defibrillation electrode 150) for delivering anti-tachyarrhythmia therapy to atrium 110. First lead 125 and proximal defibrillation electrode 150 are proportioned for disposing defibrillation electrode 150 in the supraventricular region of heart 105. Proximal defibrillation electrode 150 is disposed in atrium 110, superior vena cava 155, or in both atrium 110 and superior vena cava 155 in the various embodiments of cardiac rhythm management system 100. Thus, cardiac rhythm management system 100 allows the delivery of both atrial and ventricular anti-tachyarrhythmia therapy from a single first lead 125, rather than from multiple leads.

Another advantage of cardiac rhythm management system 100 is that placement of proximal defibrillation electrode 150 in a coronary sinus/great vein is avoided, which greatly eases the lead placement procedure by the implanting physician. Cardiac rhythm management system 100 further recognizes and distinguishes between atrial tachyarrhythmia activity and ventricular tachyarrhythmia activity, and provides particularized anti-tachyarrhythmia therapy in response to each chamber's tachyarrhythmia activity. As described above, the anti-tachyarrhythmia therapy provided to heart 105 may comprise different energy levels in response to atrial tachyarrhythmia activity than in response to ventricular tachyarrhythmia activity. Countershock waveforms, the delay in providing therapy, and other therapy parameters may also differ depending upon whether atrial or ventricular tachyarrhythmia activity is detected.

Thus, the cardiac rhythm management system 100 provides either atrial or both atrial and ventricular anti-tachyarrhythmia therapy through a single endocardial lead, although a separate lead may also be used, such as for sensing heart activity. In addition to providing dual-chamber anti-tachyarrhythmia therapy through a single endocardial lead, the cardiac rhythm management system 100 avoids the need for the difficult placement of an electrode in the coronary sinus/great vein region. As a result, the convenience of the lead placement procedure by the implanting physician is greatly increased.

It is to be understood that the above description is intended to be illustrative, and not restrictive. Many other embodiments will be apparent to those of skill in the art upon reviewing the above description. The scope of the invention should, therefore, be determined with reference to the appended claims, along with the full scope of equivalents to which such claims are entitled.

What is claimed is:

1. An implantable device comprising:
    a first connector, for a first supraventricular electrode that is proportioned for disposition on an intravascular lead within a supraventricular region of the heart;
    a second connector, for a first ventricular electrode that is proportioned for disposition on the same intravascular lead within a ventricle of the heart;

wherein the device permits delivering atrial anti-tachyarrhythmia therapy between two electrodes located on the same intravascular lead, the two electrodes consisting of the first supraventricular and first ventricular electrodes, in response to atrial heart activity indicating a need for atrial anti-tachyarrhythmia therapy; and an atrial sensor, coupled to the device, to sense the atrial heart activity indicating a need for atrial anti-tachyarrhythmia therapy, wherein the atrial sensor includes a second supraventricular electrode for sensing the atrial heart activity indicating a need for atrial anti-tachyarrhythmia therapy, and wherein the atrial sensor includes a third supraventricular electrode for sensing the atrial heart activity indicating a need for atrial anti-tachyarrhythmia therapy.

2. A system including the device of claim 1, and further comprising an intravascular lead including:

a first supraventricular electrode, proportioned for disposition on the intravascular lead within a supraventricular region of the heart; and a first ventricular electrode, proportioned for disposition on the same intravascular lead within a ventricle of the heart.

3. The device of claim 1, wherein the first connector is for a first supraventricular electrode that is proportioned for disposition on the intravascular lead within an atrium.

4. The device of claim 1, wherein the first connector is for a first supraventricular electrode that is proportioned for disposition in a superior vena cava of the patient.

5. The device of claim 1, wherein the first connector is for a first supraventricular electrode that is proportioned for disposition in a high portion of an atrium and in a superior vena cava of the patient.

6. The device of claim 1, wherein the device permits delivering ventricular anti-tachyarrhythmia therapy between the two electrodes consisting of the first supraventricular and first ventricular electrodes, in response to ventricular heart activity indicating a need for ventricular anti-tachyarrhythmia therapy.

7. A system including the device of claim 1, the system further comprising a ventricular sensor, coupled to the device, for sensing ventricular heart activity including ventricular activations.

8. The system of claim 7, wherein the ventricular sensor includes a second ventricular electrode for the sensing of ventricular heart activity including ventricular activations.

9. The system of claim 7, wherein the device includes a synchronizer to synchronize the delivery of the atrial anti-tachyarrhythmia therapy to one of the ventricular activations.

10. An implantable cardiac rhythm management system for delivering atrial anti-tachyarrhythmia therapy to a heart in a patient, the device comprising:

a first supraventricular electrode, proportioned for disposition within a supraventricular region of the heart;

a first ventricular electrode, proportioned for disposition within a ventricle of the heart;

means for delivering the atrial anti-tachyarrhythmia therapy between two electrodes located on the same intravascular lead, the two electrodes consisting of the first supraventricular and first ventricular electrodes, in response to atrial heart activity indicating a need for atrial anti-tachyarrhythmia therapy; and an atrial sensor, coupled to the means for delivering the anti-tachyarrhythmia therapy, for sensing the atrial heart activity indicating a need for atrial anti-tachyarrhythmia therapy, wherein the atrial sensor includes a second supraventricular electrode for sensing the atrial heart activity indicating a need for atrial anti-tachyarrhythmia therapy, and wherein the atrial sensor includes a third supraventricular electrode for sensing the atrial heart activity indicating a need for atrial anti-tachyarrhythmia therapy.

11. The system of claim 10, wherein the means for delivering the atrial anti-tachyarrhythmia therapy delivers the atrial anti-tachyarrhythmia therapy through the first supraventricular electrode and the first ventricular electrode in response to ventricular heart activity indicating a need for ventricular anti-tachyarrhythmia therapy.

12. The system of claim 10, wherein the first supraventricular electrode is proportioned for disposition in the atrium.

13. The system of claim 10, wherein the first supraventricular electrode is proportioned for disposition in a superior vena cava of the patient.

14. The system of claim 10, wherein the first supraventricular electrode is proportioned for disposition in a high portion of an atrium and in a superior vena cava of the patient.

15. The system of claim 10, further comprising a transvenous first lead carrying each of the first supraventricular and first ventricular electrodes.

16. The system of claim 10, further comprising an endocardial first lead carrying each of the first supraventricular and first ventricular electrodes.

17. The system of claim 10, further comprising a ventricular sensor, coupled to the ICD device, for sensing ventricular heart activity including ventricular activations.

18. The system of claim 17, wherein the ventricular sensor includes a second ventricular electrode for the sensing of ventricular heart activity including ventricular activations.

19. The system of claim 17, wherein the ICD includes a synchronizer for synchronizing the delivery of the anti-tachyarrhythmia therapy to one of the ventricular activations.

20. An implantable device comprising:

a first connector, for a first supraventricular electrode that is proportioned for disposition on an intravascular lead within a supraventricular region of the heart;

a second connector, for a first ventricular electrode that is proportioned for disposition on the same intravascular lead within a ventricle of the heart;

wherein the device permits delivering atrial anti-tachyarrhythmia therapy between two electrodes located on the same intravascular lead, the two electrodes consisting of the first supraventricular and first ventricular electrodes, in response to atrial heart activity indicating a need for atrial anti-tachyarrhythmia therapy; and wherein the device permits delivering ventricular anti-tachyarrhythmia therapy, between the same two electrodes from which the atrial anti-tachyarrhythmia is delivered, in response to ventricular heart activity indicating a need for ventricular anti-tachyarrhythmia therapy, and wherein the ventricular anti-tachyarrhythmia therapy includes a ventricular shock, and wherein the atrial anti-tachyarrhythmia therapy includes an atrial shock, and wherein the atrial and ventricular shocks have different waveforms.

21. The device of claim 20, wherein the ventricular anti-tachyarrhythmia therapy includes a ventricular shock, and wherein the atrial anti-tachyarrhythmia therapy includes an atrial shock, and wherein the atrial and ventricular shocks have different energies.

22. A system including the device of claim 20, and further comprising an intravascular lead including:
- a first supraventricular electrode, proportioned for disposition on the intravascular lead within a supraventricular region of the heart; and
- a first ventricular electrode, proportioned for disposition on the same intravascular lead within a ventricle of the heart.

23. An implantable device comprising:
- a first connector, for a first supraventricular electrode that is proportioned for disposition on an intravascular lead within a supraventricular region of the heart;
- a second connector, for a first ventricular electrode that is proportioned for disposition on the same intravascular lead within a ventricle of the heart;
- wherein the device permits delivering atrial anti-tachyarrhythmia therapy between two electrodes located on the same intravascular lead, the two electrodes consisting of the first supraventricular and first ventricular electrodes, in response to atrial heart activity indicating a need for atrial anti-tachyarrhythmia therapy; and
- wherein the device permits delivering ventricular anti-tachyarrhythmia therapy, between the same two electrodes from which the atrial anti-tachyarrhythmia is delivered, in response to ventricular heart activity indicating a need for ventricular anti-tachyarrhythmia therapy, and wherein the ventricular anti-tachyarrhythmia therapy includes a ventricular shock, and wherein the atrial anti-tachyarrhythmia therapy includes an atrial shock, and wherein the atrial and ventricular shocks have different delays between arrhythmia detection and therapy delivery.

24. The device of claim 23, wherein the ventricular anti-tachyarrhythmia therapy includes a ventricular shock, and wherein the atrial anti-tachyarrhythmia therapy includes an atrial shock, and wherein the atrial and ventricular shocks have different energies.

25. A method comprising:
- disposing a first ventricular electrode in a ventricle of the heart using an intravascular lead;
- intravascularly disposing a first supraventricular electrode in a supraventricular region of the heart using the same intravascular lead;
- monitoring atrial heart activity for atrial tachyarrhythmia activity indicative of a need for atrial anti-tachyarrhythmia therapy;
- monitoring ventricular heart activity for ventricular tachyarrhythmia activity indicative of a need for ventricular anti-tachyarrhythmia therapy;
- applying, between the same first supraventricular and first ventricular electrodes on the same intravascular lead:
  (1) the atrial anti-tachyarrhythmia therapy to the heart if atrial tachyarrhythmia activity needing atrial anti-tachyarrhythmia therapy is detected; and (2) the ventricular anti-tachyarrhythmia therapy to the heart if ventricular tachyarrhythmia activity needing ventricular anti-tachyarrhythmia therapy is needed, and in which the atrial anti-tachyarrhythmia therapy and the ventricular anti-tachyarrhythmia therapy each include shocks, wherein the anti-tachyarrhythmia therapy shock includes a different waveform than the ventricular anti-tachyarrhythmia therapy shock.

26. The method of claim 25, in which the atrial anti-tachyarrhythmia therapy and the ventricular anti-tachyarrhythmia therapy each include shocks, wherein the anti-tachyarrhythmia therapy shock includes a different energy than the ventricular anti-tachyarrhythmia therapy shock.

27. A method comprising:
- disposing a first ventricular electrode in a ventricle of the heart using an intravascular lead;
- intravascularly disposing a first supraventricular electrode in a supraventricular region of the heart using the same intravascular lead;
- monitoring atrial heart activity for atrial tachyarrhythmia activity indicative of a need for atrial anti-tachyarrhythmia therapy;
- monitoring ventricular heart activity for ventricular tachyarrhythmia activity indicative of a need for ventricular anti-tachyarrhythmia therapy;
- applying, between the same first supraventricular and first ventricular electrodes on the same intravascular lead:
  (1) the atrial anti-tachyarrhythmia therapy to the heart if atrial tachyarrhythmia activity needing atrial anti-tachyarrhythmia therapy is detected: and (2) the ventricular anti-tachyarrhythmia therapy to the heart if ventricular tachyarrhythmia activity needing ventricular anti-tachyarrhythmia therapy is needed; and
- in which the atrial anti-tachyarrhythmia therapy and the ventricular anti-tachyarrhythmia therapy each include shocks, wherein the anti-tachyarrhythmia therapy shock includes a different delay between arrhythmia detection and shock delivery than the ventricular anti-tachyarrhythmia therapy shock.

28. The method of claim 27, in which the atrial anti-tachyarrhythmia therapy and the ventricular anti-tachyarrhythmia therapy each include shocks, wherein the anti-tachyarrhythmia therapy shock includes a different energy than the ventricular anti-tachyarrhythmia therapy shock.

* * * * *

UNITED STATES PATENT AND TRADEMARK OFFICE
CERTIFICATE OF CORRECTION

| | | |
|---|---|---|
| PATENT NO. | : 7,103,409 B2 | Page 1 of 1 |
| APPLICATION NO. | : 10/434612 | |
| DATED | : September 5, 2006 | |
| INVENTOR(S) | : Warren | |

It is certified that error appears in the above-identified patent and that said Letters Patent is hereby corrected as shown below:

In column 12, line 35, in Claim 27, delete "detected:" and insert -- detected; --, therefor.

Signed and Sealed this

Fifth Day of December, 2006

JON W. DUDAS
*Director of the United States Patent and Trademark Office*